(12) United States Patent
Levy

(10) Patent No.: US 7,795,439 B2
(45) Date of Patent: Sep. 14, 2010

(54) IN-SITU TREATMENT OF PYRIDINE 2,3-DICARBOXYLIC ACID ESTERS WITH AN OXIDIZING AGENT

(75) Inventor: Michael A. Levy, Hannibal, MO (US)

(73) Assignee: BASF Aktiengesellschaft, Ludwigshafen (DE)

( * ) Notice: Subject to any disclaimer, the term of this patent is extended or adjusted under 35 U.S.C. 154(b) by 703 days.

(21) Appl. No.: 10/563,207

(22) PCT Filed: Jun. 25, 2004

(86) PCT No.: PCT/EP2004/006893

§ 371 (c)(1),
(2), (4) Date: Jun. 30, 2006

(87) PCT Pub. No.: WO2005/005391

PCT Pub. Date: Jan. 20, 2005

(65) Prior Publication Data

US 2007/0185331 A1 Aug. 9, 2007

(51) Int. Cl.
*C07D 401/04* (2006.01)
*C07D 213/803* (2006.01)
(52) U.S. Cl. .................... 546/274.1; 546/321
(58) Field of Classification Search .......... 546/274.1, 546/318, 321
See application file for complete search history.

(56) References Cited

U.S. PATENT DOCUMENTS

| 4,723,011 | A |   | 2/1988  | Doehner |   |
|-----------|---|---|---------|---------|---|
| 4,798,619 | A |   | 1/1989  | Los |   |
| 4,816,588 | A |   | 3/1989  | Rieker |   |
| 5,288,866 | A | * | 2/1994  | Strong | ......... 544/215 |
| 5,334,576 | A |   | 8/1994  | Doehner, Jr. et al. |   |
| 5,378,843 | A |   | 1/1995  | Strong |   |
| 5,614,635 | A |   | 3/1997  | Miller |   |
| 5,925,765 | A |   | 7/1999  | Bessard |   |
| 6,080,867 | A |   | 6/2000  | Wu |   |
| 6,133,450 | A | * | 10/2000 | Cauwenberg et al. | ....... 546/321 |

FOREIGN PATENT DOCUMENTS

GB    2192877 A  *  1/1988

OTHER PUBLICATIONS

Van Der Puy et. al., "Controlled, Regiospecific Oxidation of Pyridine Carboxylic Acids and Esters with Elemental Fluorine", Tetrahedron Letters, vol. 29, No. 35, pp. 4389-4392, 1988.*

* cited by examiner

*Primary Examiner*—Janet L. Andres
*Assistant Examiner*—Binta Robinson
(74) *Attorney, Agent, or Firm*—Rothwell, Figg, Ernst & Manbeck, P.C.

(57) ABSTRACT

A method for the in-situ treatment of a pyridine-2,3-dicarboxylic acid ester with an oxidizing agent, such as hydrogen peroxide, to improve product quality is provided. The method for the in-situ removal of impurities from a saponified solution of pyridine-2,3-dicarboxylic acid ester comprises the steps of providing a solution of pyridine-2,3-dicarboxylic acid ester, saponifying the solution with a base to form the corresponding pyridine-2,3-dicarboxylic acid salt, reacting the solution with an oxidizing agent in an amount effective to remove impurities, acidifying the solution with an acid to convert the pyridine-2,3-dicarboxylic acid into the corresponding pyridine-2,3-dicarboxylic acid, and collecting a purified solution comprising pyridine-2,3-dicarboxylic acid. Further provided is a method for the preparation of herbicidal 2-(2-imidazolin-2-yl)nicotinic acids, esters, and salts by using a pyridine-2,3-dicarboxylic acid salt prepared by the above method as an intermediate.

43 Claims, No Drawings

IN-SITU TREATMENT OF PYRIDINE 2,3-DICARBOXYLIC ACID ESTERS WITH AN OXIDIZING AGENT

CROSS REFERENCE TO RELATED APPLICATION

This application is a 35 USC 371 National Phase Entry Application from PCT/EP2004/006893, filed Jun. 25, 2004, and designating the United States, which claims the benefit of U.S. Provisional 60/484,485, filed Jul. 2, 2003.

FIELD OF THE INVENTION

The invention relates to methods for improving product quality of pyridine-2,3-dicarboxylic acids. In particular, the invention relates to the in-situ treatment of saponified pyridine-2,3-dicarboxylic acid esters with hydrogen peroxide to produce high quality diacids.

BACKGROUND OF THE INVENTION

Pyridine-2,3-dicarboxylate derivatives are useful intermediates for the preparation of herbicidal 2-(2-imidazolin-2-yl) nicotinic acids, esters, and salts. Several such herbicidal compounds are described in U.S. Pat. No. 5,334,576 and U.S. Pat. No. 4,798,619, which are incorporated by reference herein. A number of processes for the manufacture of pyridine-2,3-dicarboxylate derivatives, and their intermediates, have been described previously. For example, U.S. Pat. No. 4,723,011 provides a method for preparing pyridine-2,3-dicarboxylic acid esters by reacting an x-halo-p-ketoester with an $\alpha,\beta$-unsaturated aldehyde or ketone in the presence of an ammonium salt. U.S. Pat. No. 4,816,588 provides a method for converting 8-substituted quinolines into pyridine-2,3-dicarboxylic acid esters by batch oxidation with large stoichiometric excesses of hydrogen peroxide and base. U.S. Pat. No. 5,614,635 provides a method for the preparation of pyridine-2,3-dicarboxylic acid esters by continuous oxidation of substituted quinolines with a large stoichiometric excess of hydrogen peroxide and base. The methods provided by these patents and others in the art have been criticized as being plagued with the problems of low yield and low purity, and the use of unstable halogenated oxalacetate intermediates.

U.S. Pat. No. 6,080,867 and U.S. Pat. No. 5,925,764, both of which are incorporated by reference in their entirety herein, disclose methods of preparing pyridine-2,3-dicarboxylic acid esters that purports to solve the problems described above. According to one method, an amino alkoxy (or alkylthio)oxalacetate is reacted with an $\alpha,\beta$-unsaturated ketone in the presence of a solvent and an ammonia source. According to a second method, an amino alkoxy (or alkylthio)maleate or fumarate is reacted with an $\alpha,\beta$-unsaturated ketone in the presence of a solvent.

While these methods overcome some of the problems of the earlier synthesis methods, pyridine-2,3-dicarboxylic acid esters manufactured according to this process, and their corresponding diacids, still contain impurities that affect the quality and processing behavior of process streams, product streams, and effluent streams. In particular, when the above-described method has been implemented for full-scale manufacturing of pyridine-2,3-dicarboxylic acid analogs, such as 5-ethyl-pyridine-2,3-dicarboxylic acid, product quality issues have been observed. Especially noted quality concerns include problems with product purity, color, and odor, and problems resulting from the formation of dark tars in process waste streams. As a direct result of these product quality problems, extra processing costs must be expended to dry filter product, develop procedures to remove impurities from below-specification diester and diacid, and clean tars from effluent treatment systems.

In light of the aforementioned problems, there remains a need in the art for an improved process for the manufacture of pyridine-2,3-dicarboxylic acid wherein the impurities are removed during the manufacturing process. Such an improved process would provide an improved diacid product and reduce manufacturing costs that are unnecessarily elevated due to the requirement of removing impurities from product streams and effluent streams.

BRIEF SUMMARY OF THE INVENTION

The present invention provides a method for the in-situ treatment of a pyridine-2,3-dicarboxylic acid ester process stream with an oxidizing agent to improve product quality. In particular, it has been discovered that treating a pyridine-2,3-dicarboxylic acid ester process stream with an oxidizing agent, such as hydrogen peroxide, during the manufacturing process chemically removes impurities that would otherwise have to be later removed from product and effluent streams at a much higher cost and with much greater effort. For example, it has been found that the addition of relatively small amounts of hydrogen peroxide to a saponified diester process stream produces rapid removal of dark organic impurities.

In one aspect, the invention provides a method for the in-situ removal of impurities from a saponified solution of pyridine-2,3-dicarboxylic acid ester. This method comprises the steps of providing a process stream comprised of a saponified solution comprising pyridine-2,3-dicarboxylic acid ester and a base, reacting the solution with an oxidizing agent in an amount effective to remove impurities, thereby providing a purified saponified solution, and collecting the purified saponified solution.

According to one embodiment, the method comprises the steps of providing a solution of pyridine-2,3-dicarboxylic acid ester containing impurities, saponifying the solution by adding a base, thereby forming a saponified solution of a pyridine-2,3-dicarboxylic acid salt, reacting the solution with an oxidizing agent in an amount effective to remove the impurities, adding an acid to the solution, thereby acidifying the solution and converting the pyridine-2,3-dicarboxylic acid salt into the corresponding pyridine-2,3-dicarboxylic acid, and collecting a purified solution of pyridine-2,3-dicarboxylic acid.

In another aspect of the invention there is provided a method for the preparation of herbicidal 2-(2-imidazolin-2-yl)nicotinic acids, esters, and salts. This method comprises the steps of providing a solution of pyridine-2,3-dicarboxylic acid ester, saponifying the solution by adding a base, thereby forming a saponified solution of pyridine-2,3-dicarboxylic acid salt, reacting the solution with an oxidizing agent in an amount effective to remove the impurities, adding an acid to the solution, thereby acidifying the solution and converting the pyridine-2,3-dicarboxylic acid salt into the corresponding pyridine-2,3-dicarboxylic acid, and using the pyridine-2,3-dicarboxylic acid as an intermediate in the preparation of herbicidal 2-(2-imidazolin-2-yl)nicotinic acids, esters, and salts.

These and other features and advantages of the present invention will become more readily apparent to those skilled in the art upon consideration of the following detailed description, which describes both the preferred and alternative embodiments of the present invention.

DETAILED DESCRIPTION OF THE INVENTION

The present invention now will be described more fully hereinafter with reference to preferred embodiments of the invention. This invention may, however, be embodied in many different forms and should not be construed as limited to the embodiments set forth herein; rather, these embodiments are provided so that this disclosure will be thorough and complete, and will fully convey the scope of the invention to those skilled in the art. It should thus be understood that the invention includes numerous alternatives, modifications and equivalents as will become apparent from consideration of the following detailed description. The term "comprising" and variations thereof as used herein is used synonymously with the term "including" and variations thereof and is an open, non-limiting term.

The present invention provides a method for the in-situ treatment of a pyridine-2,3-dicarboxylic acid ester process stream with an oxidizing agent to improve product quality. As described above, various methods are known in the art for preparing pyridine-2,3-dicarboxylic acid ester. Particularly relevant to the present invention are the methods described in U.S. Pat. No. 6,080,867 and U.S. Pat. No. 5,925,764. One method involves the reaction of an amino alkoxy (or alkylthio)oxalacetate with an α,β-unsaturated ketone in the presence of a solvent and an ammonia source. This method can be illustrated as shown below in flow diagram I.

Flow Diagram I

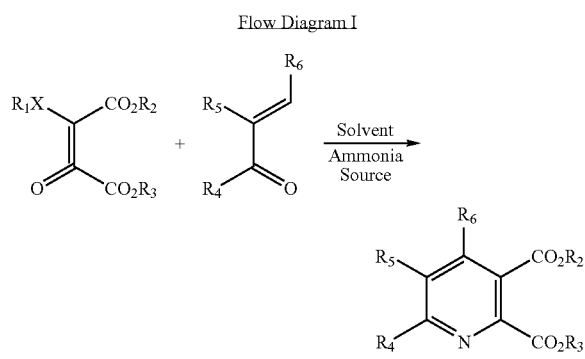

wherein X is O or S; $R_1$ is $C_1$-$C_6$ alkyl, phenyl or substituted phenyl; $R_2$ and $R_3$ are each independently $C_1$-$C_6$ alkyl, phenyl or substituted phenyl; $R_4$ and $R_6$ are each independently H, $C_1$-$C_6$ alkyl, $C_1$-$C_6$ alkenyl, phenyl or substituted phenyl; and $R_5$ is H, halogen, $C_1$-$C_6$ alkyl optionally substituted with one or more $C_1$-$C_4$ alkoxy groups, $C_1$-$C_6$ alkenyl, phenyl, or substituted phenyl. Another method involves the reaction of an amino alkoxy (or alkylthio)maleate or fumarate with an α,β-unsaturated ketone in the presence of a solvent. This method can be illustrated as shown below in flow diagram II.

Flow Diagram II

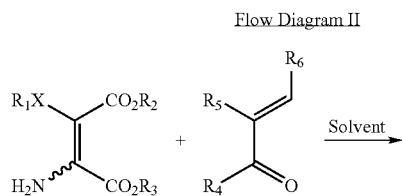

-continued

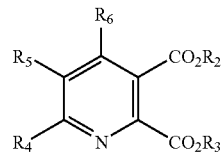

wherein X and $R_1$-$R_6$ are as described above.

The present invention, however, provides a method for the preparation of pyridine-2,3-dicarboxylic acid that includes a distinct improvement over the known production methods. The improvement resides in the discovery that the addition of an oxidizing agent, such as hydrogen peroxide ($H_2O_2$), to a process stream during the manufacturing of the product chemically removes impurities from the product.

In the manufacture of pyridine-2,3-dicarboxylic acid according to the prior known methods, impurities remain in the product and effluent streams and must be removed, leading to increased process complexity and cost. Addition of an oxidation treatment step to the prior known method described above has been shown to produce higher quality diacids, which also improves the manufacturing process of additional products made using pyridine-2,3-dicarboxylic acids as intermediates, such as imidazolinone herbicides.

The purified pyridine-2,3-dicarboxylic acid of the present invention can be used according to prior known methods in the preparation of herbicidal 2-(2-imidazolin-2-yl)nicotinic acids, esters, and salts, such as the methods provided in U.S. Pat. No. 5,334,576, which is incorporated by reference herein in its entirety.

Accordingly, the present invention provides a method for the in-situ treatment of a pyridine-2,3-dicarboxylic acid ester process stream with an oxidizing agent to improve product quality. In one preferred embodiment of the invention, the method comprises the steps of providing a process stream comprised of a saponified solution comprising a pyridine-2,3-dicarboxylic acid ester and a base, reacting the solution with an oxidizing agent in an amount effective to remove impurities, thereby providing a purified saponified solution, and collecting the purified saponified solution.

It is well known in the art that esters are hydrolyzed, either by aqueous base or aqueous acid, to yield carboxylic acid plus alcohol. A general scheme for such a reaction is shown below in flow diagram III.

Flow Diagram III

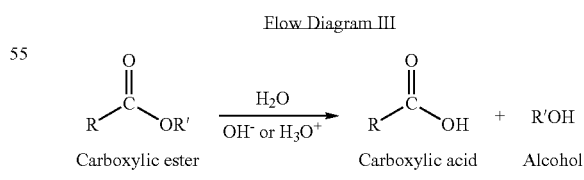

Ester hydrolysis with a base is known to have an intermediate step wherein a salt of the carboxylic acid is formed. The final carboxylic acid product is formed upon the addition of an acid. The entire scheme for a base-promoted ester hydrolysis would be understood to proceed according to flow diagram IV.

Flow Diagram IV

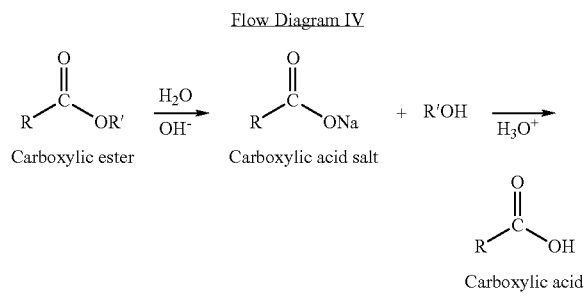

Carboxylic ester → Carboxylic acid salt + R'OH → Carboxylic acid

Ester hydrolysis in a basic solution is generally known by the common phrase "saponification," and is commonly used in the art to convert an ester, such as pyridine-2,3-dicarboxylate, into the corresponding acid. Any base effective in achieving hydrolysis of an ester into its corresponding carboxylic acid could be used in the method of the present invention. Generally, strong bases capable of producing water-soluble salts can be used, and hydroxides, such as sodium hydroxide (NaOH) and potassium hydroxide (KOH), have been found particularly useful in the present invention. Other bases useful according to the method of the present invention would be readily apparent to one of ordinary skill in the art and therefore are also contemplated by the present invention. The action of hydrolysis of an ester to form the corresponding carboxylic acid is generally understood to require the acid or base used for hydrolysis to be in an aqueous solution. It is thus understood that the saponified solution of the present invention would also include an aqueous component. Further, a saponified ester is fully converted to the corresponding carboxylic acid through an acidification step following the hydrolysis. Any acid useful in a common acidification process can be used according to the method of the present invention. Particularly preferred is sulfuric acid ($H_2SO_4$).

A process stream wherein saponification of an ester is performed is referred to herein as an aqueous saponification process stream. Further, a pyridine-2,3-dicarboxylic acid ester processed through such a stream could be referred to as a saponified diester, or, in a method where sodium hydroxide is used as the saponification base, as a NaOH-saponified diester. As the saponification step hydrolyzes the diester into a diacid salt, the process stream wherein the saponification reaction occurs would be expected to contain a mixture of diester and the corresponding diacid salt. A further acidification step could then be used to prepare the final diacid product.

The method of the present invention comprises an additional processing step that involving introduction of an oxidization agent before final product isolation, which removes impurities from the product stream. This added step involves the addition of an effective amount of an oxidizing agent to a selected process stream containing a saponified diester. As used herein, an "oxidizing agent" is an agent that participates in an oxidation-reduction reaction with a reducing agent, wherein electrons are transferred from the reducing agent to the oxidizing agent. The phrase "effective amount" as used herein is intended to refer to an amount that has the desired effect of chemically removing impurities normally found in the diester process stream. Any known oxidizing agent would be expected to be useful according to the method of the present invention; however, oxidizing agents commonly known in the art as peroxides and peroxyacids have been found to be particularly effective. Peroxides are compounds that, when in a solution, provide ions comprised of two oxygen atoms (having an overall charge of −2), and can be structurally shown as $O_2^{2-}$. A common example of a peroxide is hydrogen peroxide ($H_2O_2$). Peroxyacids are acids derived from hydrogen peroxide and also provide an $O_2^{2-}$ group in solution. Examples of peroxyacids that could be used according to the present invention are peracetic acid ($CH_3COOOH$) and perbenzoic acid ($C_6H_5COOOH$). Additionally, hypohalite salts, such as sodium hypochlorite (NaOCl) or sodium hypobromite (NaOBr), are also contemplated as oxidizing agents useful according to the present invention. Strong oxidizers, such as chromates, could also be used in the method of the present invention so long as the oxidization was not allowed to proceed to the point of oxidizing the alkyl portion of the diacid molecule.

In one embodiment of the present invention, it has been found that relatively small amounts of oxidizer are required to be effective at removing the impurities. For example, when hydrogen peroxide is used as the oxidizer, ratios in the range of about 0.1 to about 2.0 moles of $H_2O_2$ per mole of diester, preferably about 0.2 to about 0.8 moles of $H_2O_2$ per mole of diester, have been found effective for removing impurities.

The method according to the present invention is easily adaptable to any known method of preparing pyridine-2,3-dicarboxylic acid, especially methods, such as those described above, wherein pyridine-2,3-dicarboxylic acid ester is prepared. As would be readily understood by one of ordinary skill in the art, processing conditions (such as temperature, amount of oxidizer, reaction time, and added shear) should generally be considered as a whole when establishing preferred ranges individually. For example, it would be expected that reaction temperature would have an effect on the amount of oxidizer necessary to remove the impurities, and vice versa. Further, the amount of impurities present in the saponified solution is another factor that must be considered when determining the amount of oxidizing agent required and the process conditions that should be utilized. In one particular embodiment, an effective processing temperature has been found to be in the range of from about 60° C. to about 110° C.

The rate of addition of the oxidizer to the saponified diester process stream can also affect the purity of the resultant diacid product. According to one embodiment of the present invention, removal of impurities normally present in the product and effluent streams associated with the method described above is generally achieved when the oxidizer is added over a period of about 15 minutes to about 120 minutes. Additionally, it has been found useful to allow additional reaction time after addition of the oxidizer to the saponified diester process stream in order to allow for removal of any residual oxidizing agent. Further, adding shear to the solution, such as in the form of stirring or other similarly effective method of agitation, has also been found useful. In one embodiment of the present invention, the added reaction time after addition of the oxidizer in association with the added shear is preferably sustained for a period of about 15 minutes to about 120 minutes.

It is generally desirable to add the oxidizing agent and stir the reaction mixture over a period that both minimizes cycle time (increasing productivity) and minimizes foaming of the reaction mixture. Additionally, it would be expected that conditions, such as temperature, time of addition, and stirring time, would be different for a continuous process than for a batch process. Optimization of such parameters would be expected to be readily apparent to one of ordinary skill in the art without undue experimentation.

It is commonly understood that a by-product of the saponification step is an alcohol corresponding to the R group removed during the hydrolysis step. See flow diagram III above. For example, saponification of a simple ester, such as ethyl propanoate, would be readily understood by one of ordinary skill in the art to produce propanoic acid and, as a by-product, ethanol. The production of such alcohol by-products would be similarly expected in the saponification of a diester as described above. When performed according to the method of the present invention, alcohol by-products can be present during the chemical removal of the impurities through addition of the oxidizing agent and be later removed during isolation of the diacid product, or the alcohol by-product can be removed prior to the addition of the oxidizing agent. Removal of the alcohol by-product, whether before or after addition of the oxidizing agent, can be performed by any method readily apparent to one of ordinary skill in the art, such as by distillation.

Typically, the diester to be treated according to the present invention has a purity level of about 85 to about 92%. Following treatment according to the present invention, the resulting diacid product typically has a purity of at least about 97%, more preferably at least about 98%. Due to the impurities normally found in a pyridine-2,3-dicarboxylic acid ester saponification mixture, the solution is generally a dark or black color. Chemical removal of the impurities through the addition of the oxidizing agent can usually be visually detected by a color change in the saponification mixture. A color change from black to a lighter tint, such as a light amber color, will generally indicate that the chemical removal of the impurities is substantially complete, and the mixture can be tested to confirm that residual oxidizing agent is not present. Such testing method would be immediately recognizable to one of ordinary skill in the art. For example, when hydrogen peroxide is used as the oxidizing agent, standard testing strips, such as KI/starch paper, could be used.

The purified saponification mixture can then be further processed depending upon the desired end-product. For example, purified diacid salt, as described above, could be isolated and recovered. Alternatively, acidification could be performed and the purified pyridine-2,3-dicarboxylic acid could be isolated and recovered. According to either recovery, known recovery and isolation procedures that would be readily apparent to one of ordinary skill in the art could be used.

The method according to the present invention is capable of providing a product stream that is essentially free from problematic impurities, and also capable of providing effluent streams that are essentially free from impurities. As the recycle and reuse of the filtrate from the washed product, as well as other effluent streams, is common in large scale manufacturing of pyridine-2,3-dicarboxylic acid and ester, the impurities in the product are also susceptible to recycling. This leads to an amplification effect wherein impurities are being introduced into the process stream through recycled filtrate as well as being produced anew during the esterification process. The method of the present invention also solves this problem, though, as the impurities are removed during manufacturing rather than after product recovery. Thus, the present invention also contemplates a method for removing impurities from a pyridine-2,3-dicarboxylic acid manufacturing process such that the resultant effluent streams, filtrates, and process by-products are essentially free from impurities.

As the introduction of the oxidizing agent is effective at removing impurities during the manufacturing process, particularly in a saponified diester process stream, a further embodiment of the present invention is a method for the preparation of pyridine-2,3-dicarboxylic acid salt that are essentially free from impurities. According to this embodiment of the invention, the method comprises providing a process stream comprising a saponified solution of pyridine-2,3-dicarboxylic acid ester, reacting the saponified solution with an oxidizing agent in an amount effective to remove impurities, and recovering the essentially pure pyridine-2,3-dicarboxylic acid salt.

As described previously, the saponified esters form carboxylic acid salts corresponding to the base used in the saponification. For example, a 5-ethyl-pyridine-2,3-dicarboxylate saponified with NaOH would be expected to form a 5-ethyl-pyridine-2,3-dicarboxylic acid sodium salt. The intermediate salt in the process stream could be recovered as a product or recovered for later use in preparing other compounds, including carboxylic acids. Alternatively, the diacid salt could be allowed to remain in the process stream for later conversion to the carboxylic acid through acidification. While such salt can be produced according to the prior known methods disclosed above, the diacid salt is still plagued with the undesirable impurities formed during the preparation of the diester. The method according to the present invention solves this problem through the addition of an oxidizing agent to the saponification solution. The impurities are removed from the saponified solution in situ, normally prior to the acidification of the diacid salt. Thus, pyridine-2,3-dicarboxylic acid salt that is essentially free from impurities can be prepared.

In yet another aspect, the present invention provides a method for the preparation of herbicidal 2-(2-imidazolin-2-yl)nicotinic acids, esters, and salts, such as imazethapyr. This method comprises the steps of providing a solution of pyridine-2,3-dicarboxylic acid ester, saponifying the solution by adding a base, thereby forming a saponified solution of pyridine-2,3-dicarboxylic acid salt, reacting the solution with an oxidizing agent in an amount effective to remove the impurities, adding an acid to the solution, thereby acidifying the solution and converting the pyridine-2,3-dicarboxylic acid salt into the corresponding pyridine-2,3-dicarboxylic acid, and using the pyridine-2,3-dicarboxylic acid as an intermediate in the preparation of herbicidal 2-(2-imidazolin-2-yl) nicotinic acids, esters, and salts. The processing steps that may be utilized to form such herbicides with a pyridine-2,3-dicarboxylic acid intermediate are well known in the art. For example, the diacid can be converted to the corresponding anhydride using a dehydrating agent, and the anhydride can be used in the reaction scheme described in U.S. Pat. Nos. 4,658,030 and 4,782,157, which are incorporated by reference herein.

EXPERIMENTAL

The present invention is more fully illustrated by the following example, which is set forth to illustrate the present invention and is not to be construed as limiting thereof.

Example I

A saponification mixture of crude diester (100 grams), water (103 grams), and 50% NaOH (76 grams) was heated to 100° C. The alcohol distillate by-product of the saponification mixture was collected (33 grams). This was followed by the slow addition of 30 grams of 35% $H_2O_2$ to the diacid salt solution over 1 hour, maintaining the temperature at 95° C. The solution was initially black in color. Addition of the $H_2O_2$ caused foaming. Foaming and reaction color were both markedly reduced as the addition of the $H_2O_2$ proceeded. After addition of all $H_2O_2$, the solution was stirred for 2 hours while maintaining a temperature of 95° C. This was followed by testing for residual peroxide using KI/starch paper, which tested negative. Water was then added (67 grams) to the oxidized solution.

The product was isolated by precipitation and the filtercake was washed with $H_2O$ (50 grams). The wet filtercake had a mass of 76.3 grams, and the mother liquor (310 grams) containing 4.0% diacid was recycled. The resulting off-white filtercake was dried overnight. The dried recovered diacid product had a mass of 61.0 grams at 98.9% purity.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed herein and that modifications and other embodiments are intended to be included within the scope of the appended claims. Although specific terms are employed herein, they are used in a generic and descriptive sense only and not for purposes of limitation.

That which is claimed:

1. A method for the in-situ removal of impurities from a saponified solution of a pyridine-2,3-dicarboxylic acid ester, said method comprising the steps of:
    providing a saponified solution comprising the product produced by adding a base to a pyridine-2,3-dicarboxylic acid ester;
    reacting said saponified solution with an amount of an oxidizing agent effective to remove impurities, thereby providing a purified saponified solution; and
    collecting said purified saponified solution;
wherein said pyridine-2,3-dicarboxylic acid ester is a compound of the formula

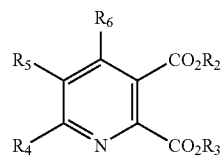

wherein $R_4$ and $R_6$ are each independently H, $C_1$-$C_6$ alkyl, $C_1$-$C_6$ alkenyl, phenyl or substituted phenyl;
$R_5$ is H; halogen; $C_1$-$C_6$ alkyl optionally substituted with one or more $C_1$-$C_4$ alkoxy groups; $C_1$-$C_6$ alkenyl; phenyl or substituted phenyl; and
$R_2$ and $R_3$ are each independently $C_1$-$C_6$ alkyl, phenyl or substituted phenyl; and
wherein said oxidizing agent is selected from the group consisting of peroxides, peroxyacids, and hypohalite salts.

2. The method of claim 1 wherein said base is a hydroxide.
3. The method of claim 2 wherein said hydroxide is sodium hydroxide.
4. The method of claim 1 wherein said oxidizing agent is hydrogen peroxide.
5. The method of claim 1 wherein said oxidizing agent is sodium hypochlorite or sodium hypobromite.
6. The method of claim 4 wherein said amount of hydrogen peroxide effective to remove impurities is an amount in the range of about 0.1 to about 2.0 moles hydrogen peroxide per mole of pyridine-2,3-dicarboxylic acid ester.
7. The method of claim 4 wherein said amount of hydrogen peroxide effective to remove impurities is an amount in the range of about 0.2 to about 0.8 moles hydrogen peroxide per mole of pyridine-2,3-dicarboxylic acid ester.
8. The method of claim 1 further comprising adding oxidizing agent until the color of said saponified solution changes from a darker color to a lighter color.
9. The method of claim 8 wherein the color of said saponified solution is changed from black to light amber.
10. The method of claim 1 wherein said reaction is performed at a temperature of about 60° C. to about 110° C.
11. The method of claim 1 wherein said oxidizing agent is added over a time period of about 15 to about 120 minutes.
12. The method of claim 1 wherein said reaction further comprises stirring said saponified solution.
13. The method of claim 12 wherein said stirring is carried out for a time period of about 15 to about 120 minutes.
14. A method for the in-situ removal of impurities from a solution of pyridine-2,3-dicarboxylic acid ester, said method comprising the steps of:
    providing a solution comprising a pyridine-2,3-dicarboxylic acid ester;
    saponifying said solution by adding a base thereto, thereby forming a saponified solution comprising a pyridine-2,3-dicarboxylic acid salt;
    reacting said saponified solution with an amount of an oxidizing agent effective to remove impurities, to produce a purified saponified solution;
    acidifying said purified saponified solution and converting said pyridine-2,3-dicarboxylic acid salt into the corresponding pyridine-2,3-dicarboxylic acid by adding an acid to said purified saponified solution; and
    collecting a purified solution comprising the pyridine-2,3-dicarboxylic acid;
wherein said pyridine-2,3-dicarboxylic acid ester is a compound of the formula

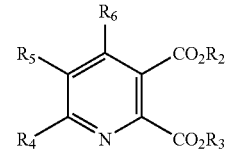

wherein $R_4$ and $R_6$ are each independently H, $C_1$-$C_6$ alkyl, $C_1$-$C_6$ alkenyl, phenyl or substituted phenyl;
$R_5$ is H; halogen; $C_1$-$C_6$ alkyl optionally substituted with one or more $C_1$-$C_4$ alkoxy groups; $C_1$-$C_6$ alkenyl; phenyl or substituted phenyl; and
$R_2$ and $R_3$ are each independently $C_1$-$C_6$ alkyl, phenyl or substituted phenyl; and
wherein said oxidizing agent is selected from the group consisting of peroxides, peroxyacids, and hypohalite salts.

15. The method of claim 14 wherein said base is a hydroxide.
16. The method of claim 15 wherein said hydroxide is sodium hydroxide.
17. The method of claim 14 wherein said oxidizing agent is hydrogen peroxide.
18. The method of claim 14 wherein said oxidizing agent is sodium hypochlorite or sodium hypobromite.
19. The method of claim 17 wherein said amount of hydrogen peroxide effective to remove impurities is an amount in the range of about 0.1 to about 2.0 moles hydrogen peroxide per mole of pyridine-2,3-dicarboxylic acid ester.

20. The method of claim 17 wherein said amount of hydrogen peroxide effective to remove impurities is an amount in the range of about 0.2 to about 0.8 moles hydrogen peroxide per mole of pyridine-2,3-dicarboxylic acid ester.

21. The method of claim 14 wherein said amount of oxidizing agent effective to remove impurities is an amount necessary to change the color of said saponified solution from a darker color to a lighter color.

22. The method of claim 21 wherein the color of said saponified solution is changed from black to light amber.

23. The method of claim 14 wherein said reaction is performed at a temperature of about 60° C. to about 110° C.

24. The method of claim 14 wherein said oxidizing agent is added over a time period of about 15 to about 120 minutes.

25. The method of claim 14 wherein said reaction further comprises stirring said saponified solution.

26. The method of claim 25 wherein said stirring is carried out for a time period of about 15 to about 120 minutes.

27. The method of claim 14 wherein said acid is sulfuric acid.

28. The method of claim 14, wherein said pyridine-2,3-dicarboxylic acid is 5-methyl-pyridine-2,3-dicarboxylic acid or 5-ethyl-pyridine-2,3-dicarboxylic acid.

29. A method for the preparation of herbicidal 2-(2-imidazolin-2-yl)nicotinic acids, esters, and salts, said method comprising the steps of:
providing a solution comprising a pyridine-2,3-dicarboxylic acid ester;
saponifying said solution by adding a base thereto, thereby forming a saponified solution comprising a pyridine-2,3-dicarboxylic acid salt;
reacting said saponified solution with an amount of an oxidizing agent effective to remove impurities to produce a purified saponified solution;
acidifying said purified saponified solution and converting said pyridine-2,3-dicarboxylic acid salt into the corresponding pyridine-2,3-dicarboxylic acid by adding an acid to said purified saponified solution;
using said pyridine-2,3-dicarboxylic acid as an intermediate in the preparation of herbicidal 2-(2-imidazolin-2-yl)nicotinic acids, esters, and salts;
wherein said pyridine-2,3-dicarboxylic acid ester is a compound of the formula

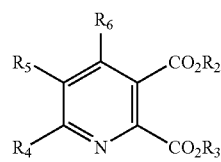

and
converting said pyridine-2,3-dicarboxylic acid into a herbicidal 2-(2-imidazolin-2-yl)nicotinic acid, ester, or salt;
wherein $R_4$ and $R_6$ are each independently H, $C_1$-$C_6$ alkyl, $C_1$-$C_6$ alkenyl, phenyl or substituted phenyl;
$R_5$ is H; halogen; $C_1$-$C_6$ alkyl optionally substituted with one or more $C_1$-$C_4$ alkoxy groups; $C_1$-$C_6$ alkenyl; phenyl or substituted phenyl; and
$R_2$ and $R_3$ are each independently $C_1$-$C_6$ alkyl, phenyl or substituted phenyl; and
wherein said oxidizing agent is selected from the group consisting of peroxides, peroxyacids, and hypohalite salts.

30. The method of claim 29 wherein said base is a hydroxide.

31. The method of claim 30 wherein said hydroxide is sodium hydroxide.

32. The method of claim 29 wherein said oxidizing agent is hydrogen peroxide.

33. The method of claim 29 wherein said oxidizing agent is sodium hypochlorite or sodium hypobromite.

34. The method of claim 32 wherein said amount of hydrogen peroxide effective to remove impurities is an amount in the range of about 0.1 to about 2.0 moles hydrogen peroxide per mole of pyridine-2,3-dicarboxylic acid ester.

35. The method of claim 32 wherein said amount of hydrogen peroxide effective to remove impurities is an amount in the range of about 0.2 to about 0.8 moles hydrogen peroxide per mole of pyridine-2,3-dicarboxylic acid ester.

36. The method of claim 29 wherein said amount of oxidizing agent effective to remove impurities is an amount necessary to change the color of said saponified solution from a darker color to a lighter color.

37. The method of claim 36 wherein the color of said saponified solution is changed from black to light amber.

38. The method of claim 29 wherein said reaction is performed at a temperature of about 60° C. to about 110° C.

39. The method of claim 29 wherein said oxidizing agent is added over a time period of about 15 to about 120 minutes.

40. The method of claim 29 wherein said reaction further comprises stirring said saponified solution.

41. The method of claim 40 wherein said stirring is carried out for a time period of about 15 to about 120 minutes.

42. The method of claim 29 wherein said acid is sulfuric acid.

43. The method of claim 29 wherein said pyridine-2,3-dicarboxylic acid is 5-methyl-pyridine-2,3-dicarboxylic acid or 5-ethyl-pyridine-2,3-dicarboxylic acid.

* * * * *